United States Patent
Gregory

(10) Patent No.: US 9,042,975 B2
(45) Date of Patent: May 26, 2015

(54) METHOD AND APPARATUS FOR ELIMINATING LOADING AND ELECTRODE POLARIZATION EFFECTS IN IMPEDANCE MEASUREMENTS FOR TISSUES AND ELECTROLYTES

(75) Inventor: William D. Gregory, Shorewood, WI (US)

(73) Assignee: WISYS TECHNOLOGY FOUNDATION, Madison, WI (US)

(*) Notice: Subject to any disclaimer, the term of this patent is extended or adjusted under 35 U.S.C. 154(b) by 865 days.

(21) Appl. No.: 13/099,068

(22) Filed: May 2, 2011

(65) Prior Publication Data

US 2011/0270066 A1 Nov. 3, 2011

Related U.S. Application Data

(60) Provisional application No. 61/343,532, filed on Apr. 30, 2010.

(51) Int. Cl.
*A61B 5/05* (2006.01)
*A61B 5/053* (2006.01)

(52) U.S. Cl.
CPC ...................... *A61B 5/053* (2013.01)

(58) Field of Classification Search
CPC .............................. A61B 5/727; A61B 5/0538
USPC ......... 600/373, 547, 393, 523, 378, 382, 391, 600/301; 607/61, 8, 17; 606/33, 41
See application file for complete search history.

(56) References Cited

U.S. PATENT DOCUMENTS

| | | | |
|---|---|---|---|
| 4,263,551 A | 4/1981 | Gregory et al. | |
| 4,493,039 A | 1/1985 | Gregory | |
| 4,881,025 A | 11/1989 | Gregory | |
| 6,522,910 B1 | 2/2003 | Gregory | |
| 6,763,263 B2 | 7/2004 | Gregory et al. | |
| 7,627,362 B2 | 12/2009 | Gregory et al. | |
| 2005/0281441 A1* | 12/2005 | Martinsen et al. | 382/124 |
| 2006/0085049 A1* | 4/2006 | Cory et al. | 607/48 |
| 2008/0009764 A1* | 1/2008 | Davies | 600/547 |
| 2009/0253193 A1 | 10/2009 | Gregory | |
| 2009/0264791 A1 | 10/2009 | Gregory et al. | |

* cited by examiner

*Primary Examiner* — Max Hindenburg
*Assistant Examiner* — Jonathan M Foreman
(74) *Attorney, Agent, or Firm* — Boyle Fredrickson, S.C.

(57) ABSTRACT

A device and method for accurately characterizing tissue impedance employs multiple electrodes at a plurality of separation distances to cancel the effects of front end loading leakage currents and electrode polarization to improve the accuracy of sensitive impedance measurements used to identify cancerous tissues. These measurements may be automated over a range of frequencies.

8 Claims, 7 Drawing Sheets

METHOD AND APPARATUS FOR ELIMINATING LOADING AND ELECTRODE POLARIZATION EFFECTS IN IMPEDANCE MEASUREMENTS FOR TISSUES AND ELECTROLYTES

CROSS REFERENCE TO RELATED APPLICATION

This application claims the benefit of U.S. provisional application Ser. No. 61/343,532, Novel Method and Apparatus for Eliminating Electrode Polarization Effects in Impedance Measurements of Tissues and Electrolytes, filed Apr. 30, 2010 and hereby incorporated by reference.

STATEMENT REGARDING FEDERALLY SPONSORED RESEARCH OR DEVELOPMENT

N/A

BACKGROUND OF THE INVENTION

The present invention relates generally to instruments for evaluating tissue in medical pathology, either ex vivo or in vivo, and in particular to a device that characterizes tissue using precise measurements of electrical impedance of the tissue.

The diagnosis of cancer and other diseases is often made by the examination of tissue samples which may be removed from the patient during a biopsy or surgical procedure or examined in vivo. These samples may be examined by a pathologist who studies these samples, including the electrical characteristics of these samples, to reach a conclusion about whether the tissue is cancerous.

The acquisition and use of impedance measurements of tissue, and the prospective usage of these measurements in the diagnosis of cancer, have been described in a number of patents including patent application Ser. No. 12/417,075, Apparatus and Method for Evaluating Ex Vivo Tissue Samples by Electrical Impedance and patent application Ser. No. 12/042,425, Method for Detecting Both Pre-Cancerous and Cancerous Tissues, both to the present inventor.

SUMMARY OF THE INVENTION

The present inventor has recognized that the extremely low voltage drops involved in the measurement of impedance of tissue at reasonable power levels make such measurements susceptible to artifacts caused by the effects of electrode polarization (EP) of the applied electrodes and the front end loading (i.e. leakage currents) of the electrical measuring devices. The present invention provides a system that may more accurately assess the impedance spectrum (i.e. complex electrical impedance as a function of frequency) of tissue.

Specifically, in a first embodiment, the present invention compensates for electrode polarization effects using an apparatus having a signal source producing an electrical signal including a range of frequencies with at least three electrodes positionable at separated points of electrical contact with the tissue. An electrical switch system connects the signal source and to different pairs the electrodes so that the electrical signal passes through different lengths of tissue and a monitoring circuit communicates with the signal source to measure the electrical signal between an electrode pair connected by the electrical switch to receive the electrical signal. An electronic computer measures the electrical signal between at least two different electrode pairs at different known separation distances to provide an impedance measurement of the tissue between at least two electrodes corrected for electrode polarization.

It is thus a feature of at least one embodiment of the invention to compensate for electrical polarization by making redundant measurements at different distances.

The electronic computer may provide the corrected impedance measurement by determining at least two points of a function relating the measurements of the electrical signal to separation distance, extrapolating the function to a separation distance of zero; and correcting the impedance measurement of the tissue between at least two electrodes using the extrapolated value of the function.

It is thus a feature of at least one embodiment of the invention to provide a simple computation using as few as two measurements to extrapolate and correct for the electrode polarization error.

The apparatus may also have a fixture for holding the at least three electrodes in a known separation pattern wherein the electronic computer determines the separation distances from stored values of the separation pattern of the fixture.

It is thus a feature of at least one embodiment of the invention to eliminate the need for a measurement of electrode separation distances during use.

The electrical switch system may be electronically controllable by the electronic computer to alternately connect the signal source to different pairs of the at least three electrodes.

It is thus a feature of at least one embodiment of the invention to provide rapid and automatic correction of electrode polarization by computer control of the electrode connections.

The apparatus may output impedance measurements for multiple frequencies of the range of frequencies.

It is thus a feature of at least one embodiment of the invention to output a description of impedance changes with frequencies thought to reveal cancerous features.

In a second embodiment, the invention corrects for amplifier loading effects in an apparatus having a tissue support and multiple electrodes including at least a driving electrode pair and a sensing electrode pair. A signal source applies an electrical signal across the driving electrodes over a range of frequencies and a monitoring circuit measures a voltage signal between the sensing electrode pair and a current signal from a measuring electrode to provide an impedance measurement of the tissue between the measuring electrode pair. The multiple electrodes are held with respect to the tissue support so that the sensing electrode pair is positioned between the driving electrode pair and there is a first separation distance between the measuring electrode and a sensing electrode proximate of the measuring electrode which is substantially less than a second separation distance between the driving electrode and the sensing electrode proximate of the measuring electrode.

It is thus a feature of at least one embodiment of the invention to provide an apparatus for characterizing tissue impedance that reduces the effect of amplifier loading. As will be described in more detail below, the close positioning of the sensing electrode and measuring electrode reduces the effect of current being drawn by the measuring amplifier.

The apparatus may also have a fixture for holding the multiple electrodes in a predetermined separation pattern.

It is thus a feature of at least one embodiment of the invention to allow rapid positioning of the electrodes for this purpose.

These particular features and advantages may apply to only some embodiments falling within the claims and thus do not define the scope of the invention.

DETAILED DESCRIPTION OF THE PREFERRED EMBODIMENT

Background

Figure 1:
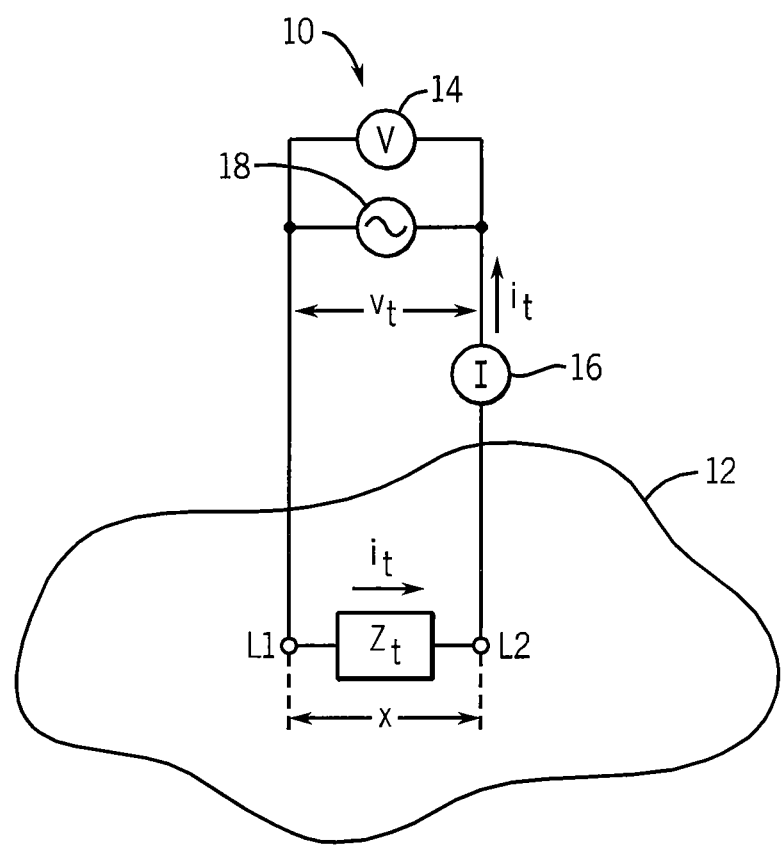
FIG. 1 is a schematic of a tissue impedance measuring apparatus.

Electrical measurements of human or animal tissue with electrically conductive electrodes have a serious measurement error that must be dealt with to obtain useful information. Because of the strong change in electrical properties at the interface between the tissue and a highly conductive electrode, the governing equations of electromagnetic theory show that there will be a build-up of electrical charge at the interface, an effect called electrode polarization (EP). Electrical conduction in the electrode is accomplished with "free" electrons, the tissues and electrolytes have the conduction electrodes bound to atoms and molecules (ions). Without special treatment of the electrode surface, the ions cannot exchange charge readily with the electrode, so this will cause buildup of unbalanced charges at the electrode-sample interface creating the EP effect.

The problem caused by the EP effect is that the presence of electrical charges on a conductive surface creates an electric field on the surface given by application of Gauss's law as:

$$E_{normal} = (q/A)/\epsilon_0$$

where $E_{normal}$ is the electric field at the surface and is normal (i.e. perpendicular) to the surface, q is the electric charge (amount of electrons) on the conductive surface, A is the surface are and epsilon is the permittivity of free space. This contribution to the total electric field in the specimen will then make a contribution to the voltage between any pair of electrodes because the voltage is just the spatial integral of the field between the electrodes:

$$\int_1^2 E^* dX = V_{1-2}$$

where $V_{1-2}$ is the voltage between points 1 and 2 in space and the product is the scalar product of the vector electric field, E, and the vector element of displacement along a path X, dX.

The contribution to E from the EP at each electrode $V_{1EP}$ $V_{2EP}$ will be included in the total field and will thus be an "extra" contribution to $V_{1-2}$. This contribution is an error that must be accounted for.

The primary way to eliminate the EP is surface treatments of the electrodes. Two types of surface treatments are used: surface coating with a chemical surface layer, and surface roughening. The two methods work on different aspects of the variables in Gauss's Law to reduce the value of $E_{normal}$: 1) by coating the electrode with a chemical that allows an exchange of the electric charge of the sample ions with the surface chemical layer, such as silver chloride (Ag—AgCl) whereby the amount of charge on the surface can be reduced; and 2) by microscopically roughening the surface, such as with "Black and Platinum" (BPt) so that the effective surface area of the sample can be increased. Note that both of these actions reduce the size of $E_{normal}$ and hence $V_{ep1-2}$. Also note that these are the only two ways that one can so something at the electrode surface to reduce the EP effect (i.e., there are only two variables to work with, charge q and area A, to reduce $E_{normal}$) and we have now exhausted the use of each variable.

Referring now to the schematic of FIG. 1, a simple "2-electrode" (aka "2-lead") impedance measuring apparatus 10 is shown with a basic tissue model. This apparatus employs a tissue sample 12 and associated measuring devices: a voltage measuring device, voltmeter 14; and a current measuring device, ammeter 16. In addition an electrical power source such as signal generator 18 (i.e. the voltage source), for example, supplies a time-varying sinusoidal voltage of a given amplitude, phase and frequency, $v_t$, via electrodes $L_1$ and $L_2$ engaged with tissue 12 at a separation distance of x. The voltmeter 14 may be used to measure the voltage $v_t$ supplied to tissue 12, or the value may be determined from the setting of the voltage source 18. The tissue 12 is modeled as having a complex tissue impedance $Z_t$ between the points of engagement of the electrodes $L_1$ and $L_2$. The complex impedance $Z_t$ is determined using the current $i_t$ amps measured by ammeter 16, and the voltage supplied by voltage source 18, $v_t$ volts, according to ohm's law:

$$Z_t = v_t/i_t \text{ (ohms)} \tag{1}$$

The measured complex impedance is with respect to the distance x and may be normalized as $Z_t/x$ to produce a measurement of, for example, ohms per millimeter. In addition, there may be a sequence of sinusoidal signals applied by signal generator 18, or the signal generator signal 18 may apply a signal having a broad spectrum such as an impulse. These approaches (and others) may be used to create an impedance spectrum $Z_t(w)$, (i.e. complex electrical impedance as a function of frequency).

However, the simple model of FIG. 1 is inadequate because the measured voltage $v_t$ across the electrodes $L_1$ and $L_2$ is not entirely applied across the tissue 12 because there may be additional voltages created by ionic electrode polarization (EP) of $L_1$ and $L_2$, $V_{1EP}$ and $V_{2EP}$ respectively. Thus, the voltage model of the tissue voltage includes these voltages in addition to the voltage dropped across the tissue material as shown by the following equation:

$$v_t = V_{1EP} + v_{material\ 1-2} + V_{2EP} \tag{2}$$

where the actual tissue voltage is represented by $v_{material\ 1-2}$.

Figure 2:
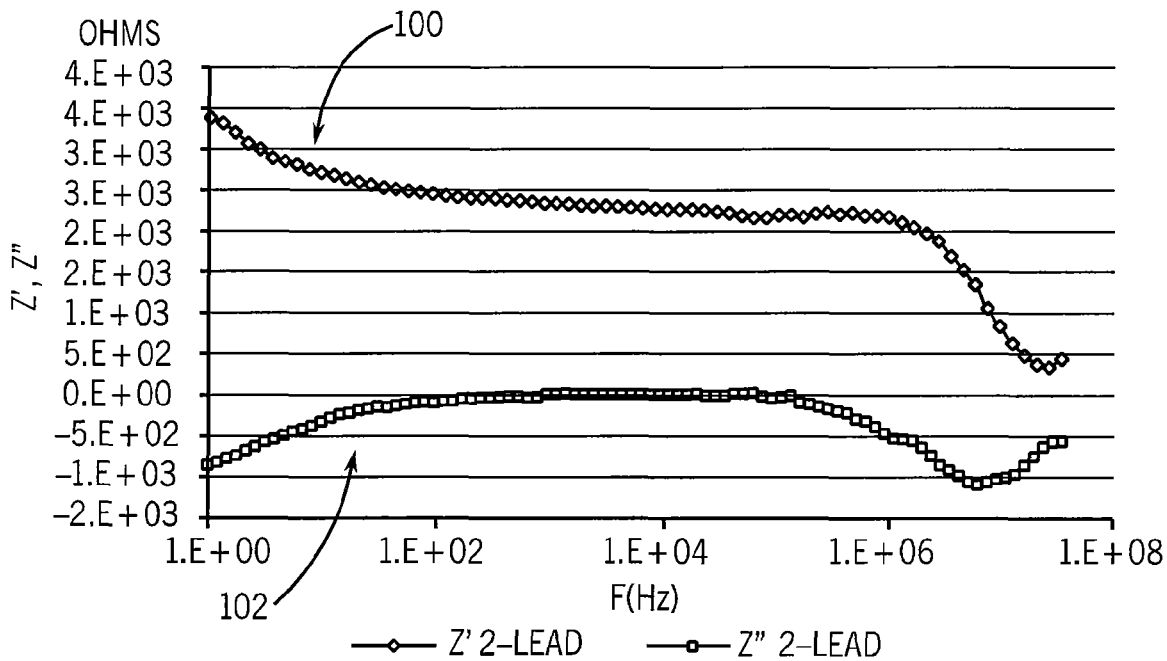
FIG. 2 is a plot of the real and imaginary portions of the tissue impedance versus frequency showing the electrode polarization effect.

This effect of EP is illustrated in FIG. 2 with data from a 2-electrode measuring apparatus. We note in FIG. 2 that at low frequencies both the real and the imaginary components of the impedance diverge in an almost exponential way as the measuring frequency approaches zero. This behavior is often cited as evidence for EP effects (even though the electrodes used in the measurement data of FIG. 2 had roughened surfaces that should reduce the polarization effects).

First Inventive Embodiment

Figure 3:
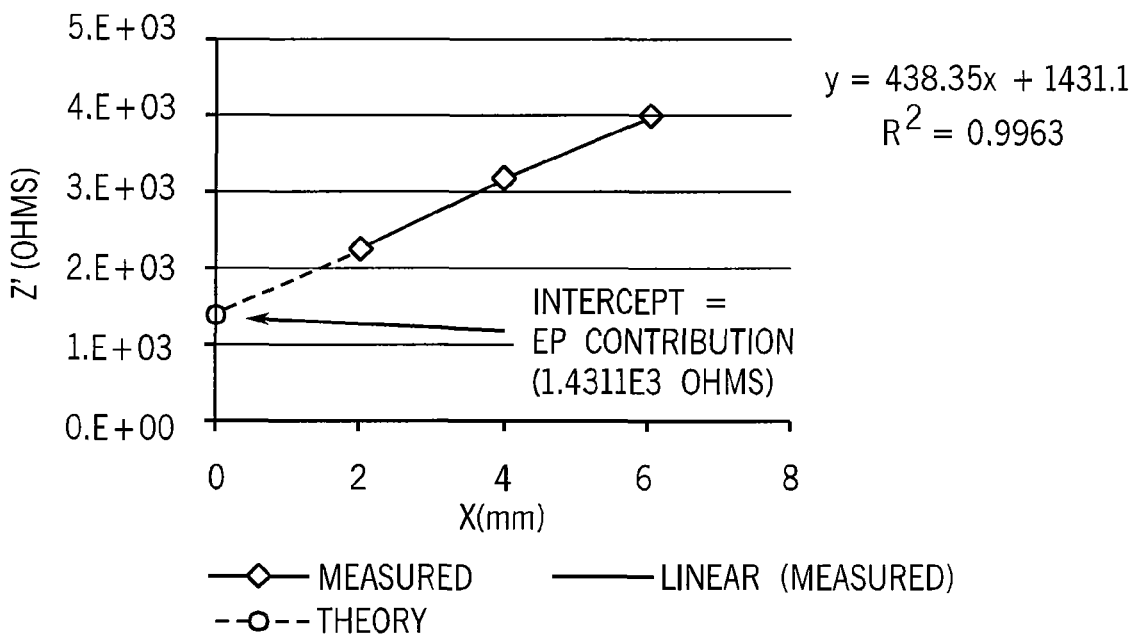
FIG. 3 is graph of real tissue impedance versus inter-electrode separation distance showing the contribution of electrode polarization to impedance at a separation distance of zero.
Figure 4:
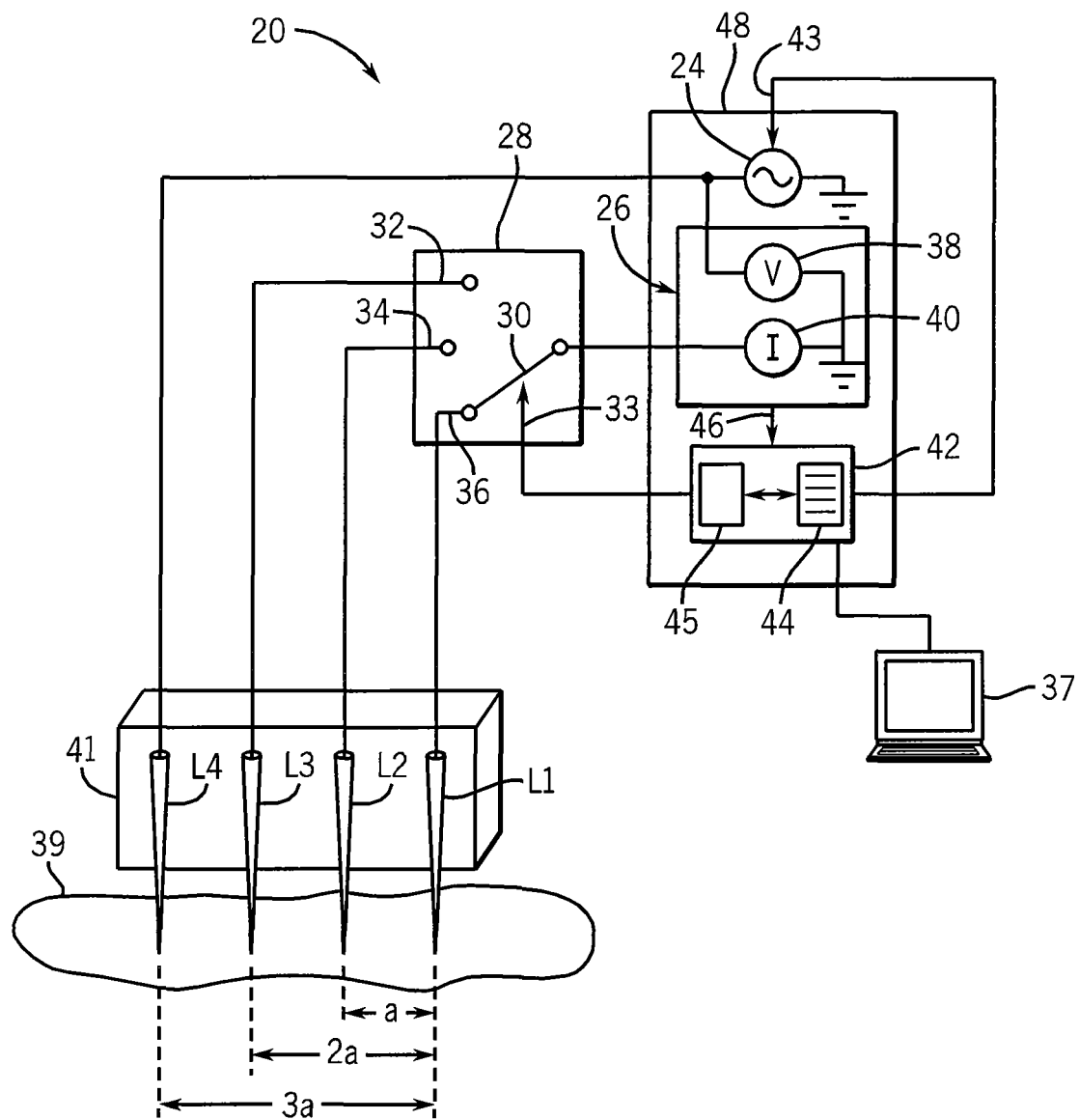
FIG. 4 is a schematic of a tissue analysis apparatus according to the present invention showing inter-electrode separation distances and electrical power switching.

The inventor recognized that while the EP voltages $V_{1EP}$, $V_{2EP}$ are essentially constant, whereas the voltage across the tissue $v_{material\,1-2}$ varies in a nearly linear relationship according to the spacing of the electrodes, x, as shown by the following equation:

$$v_{material1-2} = \rho(x/A) \quad (3)$$

where $\rho$ is the resistivity of the medium (and can be complex if both the conductivity and permittivity are of appropriate values) and A is the effective area of conduction perpendicular to the path between electrodes $L_1$ and $L_2$. This equation indicates the expected spatial dependence on x of the voltage drop across a tissue as a function of separation of the electrodes. The validity of this equation can be established by correlating the voltage across identical electrode pairs immersed in the same medium but separated by various known separation distances. FIG. 3 is a plot of just such measurements for the real part of the complex impedance, Z', (ohms) versus the electrode spacing, x, (mm) taken at 10 kHz with a saline solution measurement. Impedance data in all plots were acquired using commercially available saline solutions of 731 uS/cm using a Solartron 1260A impedance/gain-phase analyzer. The electrodes were silver wire 0.5 mm diameter coated with AgCl. The data in FIG. 4 are fit to a straight line given by $$Z = aX + b \quad (4)$$

where from equations (2) and (3) $a = \rho/A$ and $b = Z_{EP} = (V_{1EP} + V_{2EP})/i_t$. The correlation coefficient of the fit of the data to this straight line is excellent (0.9963) and is displayed on FIG. 3. Note that the intercept, b, (at x=0 mm) is the combined EP voltage contribution to the impedance measurement, $Z_{EP} = 1.4311 \times 10^3$ ohms that must be subtracted from the measured impedance to give the appropriate value of the material impedance $$Z_{material1-2} = Z_t - Z_{EP} \quad (5)$$

where $Z_t$ is the measured impedance. Thus, the present invention removes the error produced by the affect of EP on the tissue impedance measurements by calculating $Z_{EP}$ for a given current and subtracting this value from the measured impedance $Z_t$ to yield the corrected tissue impedance $Z_{material1-2}$. This is accomplished by taking at least two measurements of impedance at different electrode spacing.

The data of FIG. 3 may be taken by manually varying the inter-electrode spacing, x, while taking measurements of the separation distance and the voltage and current for at least 2 values of x. Additional data points provide additional accuracy and a preferred number of data points is at least three. The data is then used to calculate the corresponding impedances $Z_t(x)$ and estimate $Z_{EP}$ (i.e. $Z_t$ extrapolated to x=0). $Z_{EP}$ may then be used to correct the measured impedance $Z_t$ to arrive at the actual tissue impedance $Z_{material1-2}$.

An impedance spectrum $Z_{EP}(f)$ may be determined by repeating this process for different frequencies or by applying the appropriate transforms to measurements of a broad spectrum signal. In the former case, each impedance measured at each frequency $Z_t(f)$ they be corrected by the corresponding $Z_{EP}$ to yield an corrected measured tissue impedance spectrum $Z_{material1-2}(f)$ spectrum at each frequency.

Turning now to FIG. 4, an apparatus for measuring $Z_{EP}$ 20 consists of an array of four electrodes L1, L2, L3, L4 in communication with tissue 22. The electrodes may be silver wire or some other suitable electrically conductive material having a diameter of 0.5 mm and may be coated with AgCl. The electrodes may be needle electrodes, surface contact electrodes, or some combination thereof. The four electrodes L1, L2, L3, L4 may be arranged in a line in the tissue in the recited order.

Continuing with FIG. 4, an electrical switch system 28 may switch pairs of electrodes across a power source 24. This switch system 28 is shown schematically as a single pole, three pole switch. During operation, electrode pair L3-L4 may be connected across the power source 24 by pole 30 making contact with throw 32, or pair L2-L4 may be connected across the power source 24 by pole 30 making contact with throw 34, or pair L1-L4 may be connected across power source 24 by pole 30 making contact with throw 36.

In each of the above switch configurations, the signal generator 24 communicates an electrical signal of controlled voltage from a first terminal directly to electrode L4, and from a second terminal to the pole-connected electrode, (i.e. L1-L3). The signal generator 24 may provide a swept sinusoidal voltage from 0 to 108 MHz.

A monitoring circuit 26 may provide a voltmeter 38 attached across the terminals of the signal generator 24 (alternatively, the voltage may be regulated to a known quantity by the signal generator). The monitoring circuit 26 further includes an ammeter 40 or similar device connected in series between pole 30 and the terminal of the signal generator to which it is ultimately connected. The signal generator 24 and monitoring circuit 26 may be integrated into an analyzer 48, such as a Solartron 1260A impedance gain-phase analyzer commercially available from Solartron Analytical of Farnborough Hampshire United Kingdom.

Referring still to FIG. 4, the monitoring circuit 26 may provide a data interface transmitting current and voltage readings over communication channel 46 to an electronic computer 42 which may be integrated with the analyzer 48 (or a separate unit, not shown). The electronic computer 42 may have a microprocessor or programmable logic 45 and execute a stored program 44 which measures the electrical signals from the electrode pair(s) provided by monitoring circuit 26 in order to compute impedances over a range of different frequencies.

The measurements made by the electronic computer are made between at least two electrode pairs having different separation distances. For example, assuming that the electrodes are spaced uniformly from each other by a distance of a the electronic computer 42 may take measurements from lead pair L4-L3 at a separation distance of a, lead pair L4-L2 at a separation distance of 2a, and lead pair L4-L1 at a separation distance of 3a. The separation distances may be entered by a data entry device such as terminal 37. The electronic computer 42 may also control the switch 28 through control terminal 33, and the signal generator 24 through control interface 43. These measurements may be made over a range of different frequencies and used to derive impedance at each frequency. For each frequency, the measurements made at different electrode separations may be used to deduce an impedance function providing impedance as a function of electrode separation. Extrapolation of this impedance function 20 electrode separation provides the offset impedance value being an artifact of electrode polarization. The electronic computer 42 may also output impedance measurements for multiple frequencies over a range of frequencies.

The apparatus 20 may also comprise a fixture 41 for holding the electrodes in a known separation pattern wherein the electronic computer 42 determines the separation distances from stored values corresponding to the fixture 41, For example the fixture 41 may mount electrodes such as needle electrodes L1, L2, L3, L4, which may be mounted at equal distances, a, on holder 41 and configured to penetrate the tissue 39 to take the tissue impedance measurement.

As described above the 2-electrode measurement is one where the same electrodes are used to drive current through the tissue are also used to measure the voltage drop through the tissue. Another solution that reduces the induced voltage of the EP effect does so by removing the driving current from the measurement electrodes using a second pair of measuring electrodes (i.e. sensing electrodes) in the path between the current-driving electrodes (i.e. driving electrodes), which is a 4-lead (aka 4-electrode) measurement.

Figure 5:
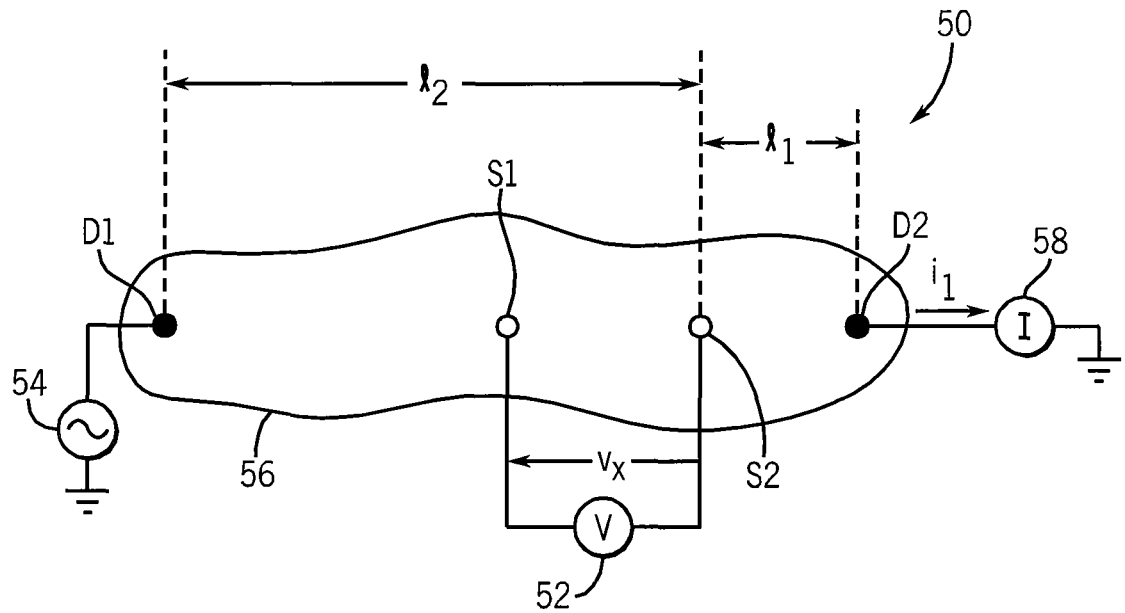
FIG. 5 is a diagram of a tissue analysis apparatus according to another embodiment of the present invention showing a 4-electrode apparatus with asymmetric inter-electrode separation distances.

FIG. 5 is an example of this type of measurement apparatus 50. In this measurement apparatus 50, four electrodes (D1,S1, S2, D2) are placed in a line in the tissue in the recited order. More specifically two voltage measuring or sensing electrodes S1, S2, are placed between two driving electrodes D1, D2.

A voltage measurement is taken of a voltage Vx across the sensing electrodes S1, S2 by a voltage measuring device, for example voltmeter 52. A signal generator 54 provides the signal to the tissue 56 across driving electrode D1, and D2 while a current measuring device such as ammeter 58 measures the current i1 through the tissue passing from driving electrode D1, and D2 as measured between electrode D2 and the signal generator 54. Note that the electrodes (D1,S1, S2, D2) are not uniformly spaced, but the sensing electrode S2 is closely proximate to the measuring electrode D2 as shown by the separation distance $l_1$ being substantially less than the separation distance $l_2$ between electrode D1 and S2. The reason for this spacing will be described further below.

Figure 6:
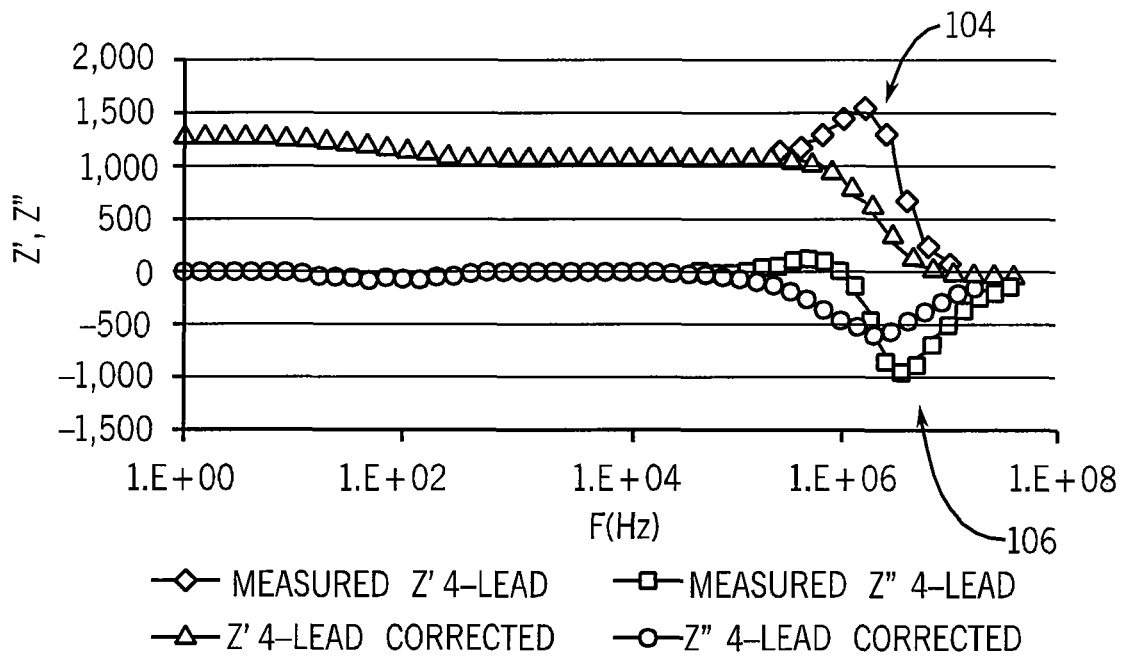
FIG. 6 is a plot of the real and imaginary portions of the tissue impedance versus frequency showing front end loading effect and the corrected plots.

The measurements taken by this apparatus 50, provide a voltage across electrodes S1, S2 and a close approximation of current between electrodes S1, S2 from which may be computed impedances Z' and Z" (real and imaginary impedances) of the tissue between the electrodes S1 and S2. A plot of these impedances as a function of frequency is shown in FIG. 6. Comparing FIG. 6 measured 4-lead data with FIG. 2, we note that the excursions in real impedance 100 and excursions in imaginary 102 at low frequencies in FIG. 2 are gone, but a new effect has appeared at higher frequencies: the real part of the impedance Z' has a noticeable peak 104, while the imaginary part Z" has a distinct wiggle in the same frequency range 106 indicating that a new source of error has been introduced.

Figure 7:
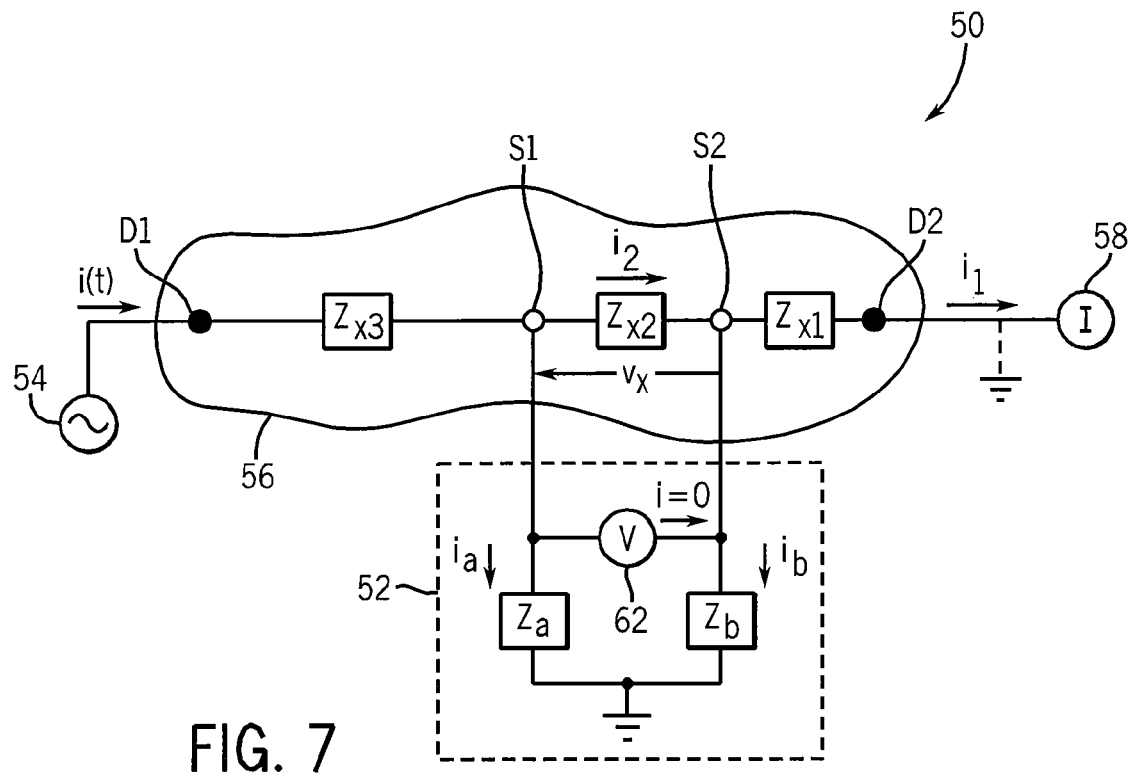
FIG. 7 is a schematic of a tissue analysis apparatus according to the embodiment of FIG. 5 demonstrating the front end loading leakage currents and showing models of the voltage measuring device and inter-electrode tissue impedances.

Turning now to FIG. 7, an electrical model of this 4-lead measurement system 50 may be used understand the source of this error. The tissue has been divided into lumped impedances $Z_{x1}$ (between electrodes D1 and S1), $Z_{x2}$ (between electrodes S1 and S2), and $Z_{x3}$ (between electrodes S2 and D2). Importantly, $Z_{x2}$ is the tissue impedance which the apparatus 50 is measuring.

The voltmeter 52 is modeled as a device 62 having front end load impedances Za, Zb to ground with associated currents $i_a$, $i_a$ respectively. Note that if the impedances Za and Zb are very large then $i_a$ and $i_b$, will approach zero. This is the ideal case wherein the input current i(t) generated by signal generator 54 into the tissue 56 will be the same current $i_1$ measured by the current measuring device 58 (which may be, for example, a transimpedance amplifier).

In effect, when these two front end loads Za, Zb are very large, it is as if the leakage currents $i_a$ and $i_b$ were not present, and the measured current $i_1$ were the same as current passing through the portion of the sample where the voltage is measured, $i_2$ (note that we define complex impedance as Z=V/I, where the bold letters indicate complex values having both a real and an imaginary components). Now consider the situation when Za and Zb are not large. In this situation the leakage currents $i_a$ and $i_b$ exist (i.e. are no longer near zero or near zero). Unfortunately, the current measured by the current measuring device is $i_1$ but the current through the portion of the specimen used to measure the voltage drop $v_x$ is $i_2$. This produces an apparent (and incorrect) impedance value of $$Z_{apparent} = v_x/i_1 \quad (6)$$

whereas the correct impedance is given by $$Z_{measured} = V_x/i_2 \quad (7)$$

To relate the apparent value, $Z_{apparent}$, to obtain the measured impedance, $Z_{measured}$, one must combine equations (6) and (7) to yield the following relation:

$$Z_{measured} = (i_2/i_1) Z_{apparent} \quad (8)$$

Using Kirchoff's Laws one can obtain the complex ratio of the current $i_2$ versus $i_1$ and substitute this in equation (8) to obtain the following expression:

$$Z_{measured} - Z_{x2}(Z_{x1} + Z_b)/Z_b = 0 \quad (9)$$

We note that when $Z_b$ is very large compared to $Z_{x1}$, equation (9) reduces to $Z_{measured} = Z_{x2}$ as expected from the arguments presented above. In general, for values of $Z_b$ that are not large compared to $Z_{x2}$, equation (9) is a complex expression that must be forced to a complex value of zero by finding the correct value of the true impedance, $Z_{x2}$. The inventor has found that the Powell procedure (using the IDL computer language) is ideal for performing this task.

Referring to FIG. 6, when this procedure is applied to the measured 4-lead impedances Z', Z" one obtains the 4-lead corrected impedances. The correction resulting in the expression of equation (9) is commonly referred to a "front end loading" correction. In FIG. 6 a second correction is also applied to the 4-lead data called the "roll-off" correction, although this correction is not as obvious unless one is looking at features near the upper limit of the impedance bridge amplifiers. The roll-off is a correction for the behavior of the amplifiers of the impedance bridge for high frequencies of the signal generator 54 near the high end of the useful range of the measuring amplifier implementing voltmeter 52. This correction is obtained using calibration 4-lead electrodes composed of high quality surface mounted resistors and capacitors that accurately model the circuit shown in FIG. 7.

Figure 8:
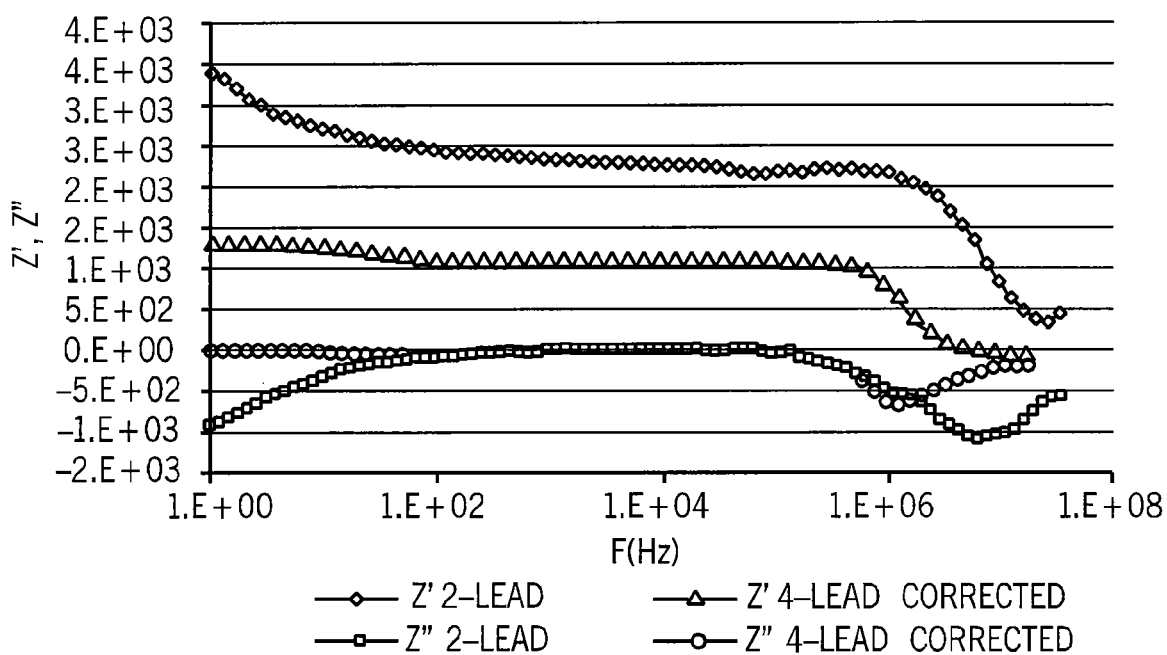
FIG. 8 is two frequency plots comparing of the real and imaginary portions of the 2-lead tissue impedance with the 4-lead corrected tissue impedance.

FIG. 8 is very instructive, because it yields an insight into the nature of the EP effect and shows the value of the 4-lead configuration. We first note that the 2-lead measurement, although it has an EP effect, has no "front end loading" effects. In the case of the 4-lead data loop currents exist but we have corrected for the loading error as shown in FIG. 8 and explained above. However, we also note that the 2-lead data show a substantial low frequency excursion in both Z' and Z", and even more surprising, we see that even above low frequencies the 2-lead Z' data show a large difference to the 4-lead Z' results of FIG. 6. Thus the common observation that the EP effect is only important at low frequencies is mistaken.

Figure 9:
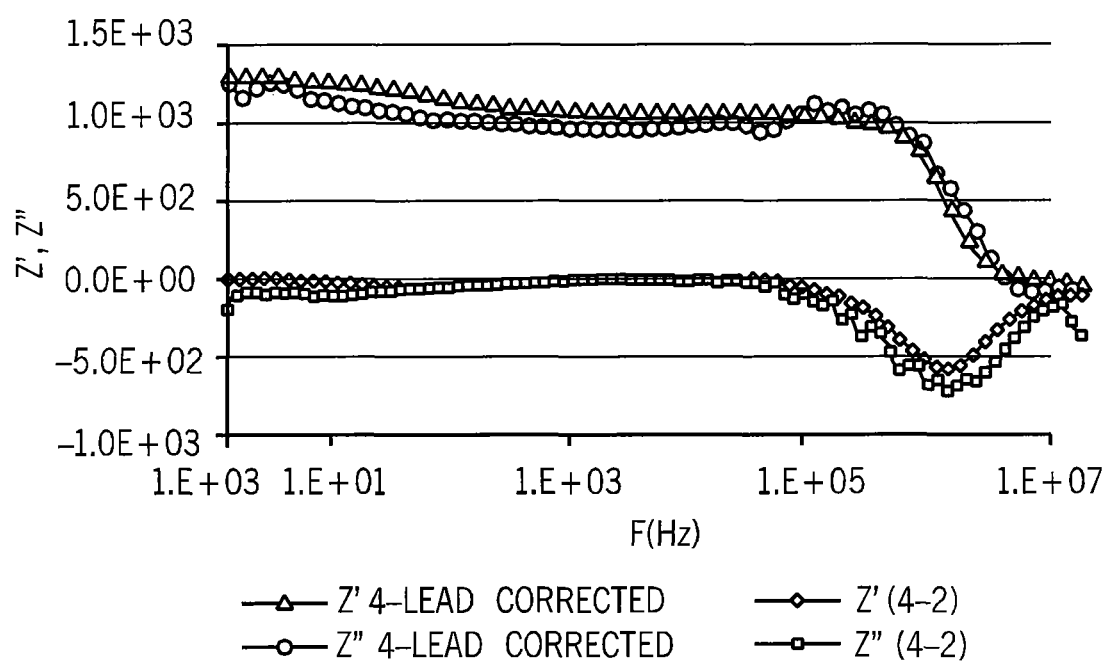
FIG. 9 is two frequency plots comparing of the real and imaginary portions of the 4-lead corrected tissue impedance with a plot of the 2-lead subtracted from the 4-lead.

Expanding on this finding, FIG. 8 shows both the 2-lead measurement with no correction for the EP effect and the 4-lead measurement with a correction for the high frequency loading and roll-off effects. We note that the real and the imaginary parts of the impedance, Z' and Z", both show an excursion away from somewhat constant values seen at higher frequencies. In addition, the real part, Z', shows a very distinct difference between the 2-lead and 4-lead measurements. Notably, the 4-lead measurement was made with a 2 mm spacing of the voltage electrodes. If one now corrects the 2-lead data by subtracting 2-lead measurements for 4 mm spacing from that of a 2 mm spacing, (leaving a net 2 mm with the EP voltage terms subtracted to zero) the plots shown in FIG. 9 are obtained, which show that the corrected 2-lead data substantially agrees with the 4-lead data over the entire frequency range. There are several observations that can be made regarding this result:

1. The low frequency excursions of the 2-lead data are due to the EP effect.
2. However, the EP effect is not limited to the low frequency range for Z'. Clearly, the large difference in Z' for the uncorrected 2 lead data and the 4-lead data are due to a huge polarization effect. This is in contrast to much of the conventional wisdom regarding the EP effect, wherein the correction for the low frequency excursions is thought to be all that is necessary to account for electrode polarization. Clearly it is not.
3. Because of analysis of the circuit of FIG. 7, it is known that the correction at higher frequencies for the 4-lead data is not needed for the 2-lead data. Because the corrected 4-lead data agree with the corrected 2-lead data, this confirms the load and roll-off corrections for 4-lead measurements.
4. This last result then means there are two ways to correct for the EP effect that are superior to electrode surface preparation alone:
   (a) 2-leads corrected by fitting the measured voltage to the separation distance of the electrode pair;
   (b) 4-lead data may be mathematically corrected for the high frequency loading and roll off effects, and
   (c) 4-lead data may be corrected by reducing the effects of front end loading by changing the relative spacing of the sensing electrodes with respect to the driving electrodes, as will be explained below.
5. Finally, while the electrodes for the measurements in this disclosure were treated to minimize EP effects, the results reported are a clear indication that surface treatment is not necessary, and that one could obtain equally good results with untreated surfaces with either the 2-lead or 4-lead version of this invention.

Returning to FIGS. 5 and 7, the inventor has found that the effect of front end loading can be reduced by changing the relative spacing of the sensing electrodes S1, S2 with respect to the driving electrodes D1, D2. This is accomplished by moving the S2 electrode closer to the D2 measuring electrode such that l1 is much less than l2 as shown in FIG. 5. This change in electrode layout effectively makes $Z_{x1}$ much less than $Z_b$ ($Z_{x1} \ll Z_b$), which reduces the amount of leakage current ib so that $i_1$ is approximately equal to $i_2$. Because $Z_{x1}$ is proportional to the distance between S2 and D2, the desired relationship can be achieved by reducing the distance between S2 and D2, hence this may be achieved, for example, when inter-electrode separation distance $l_1$ is much less than $l_2$ as shown in FIG. 5. Preferably, $l_1$ may be less than 20% of $l_2$, or $l_1$ may be less than 10% of $l_2$, or $l_1$ may be less than 5% of $l_2$.

Figure 10:
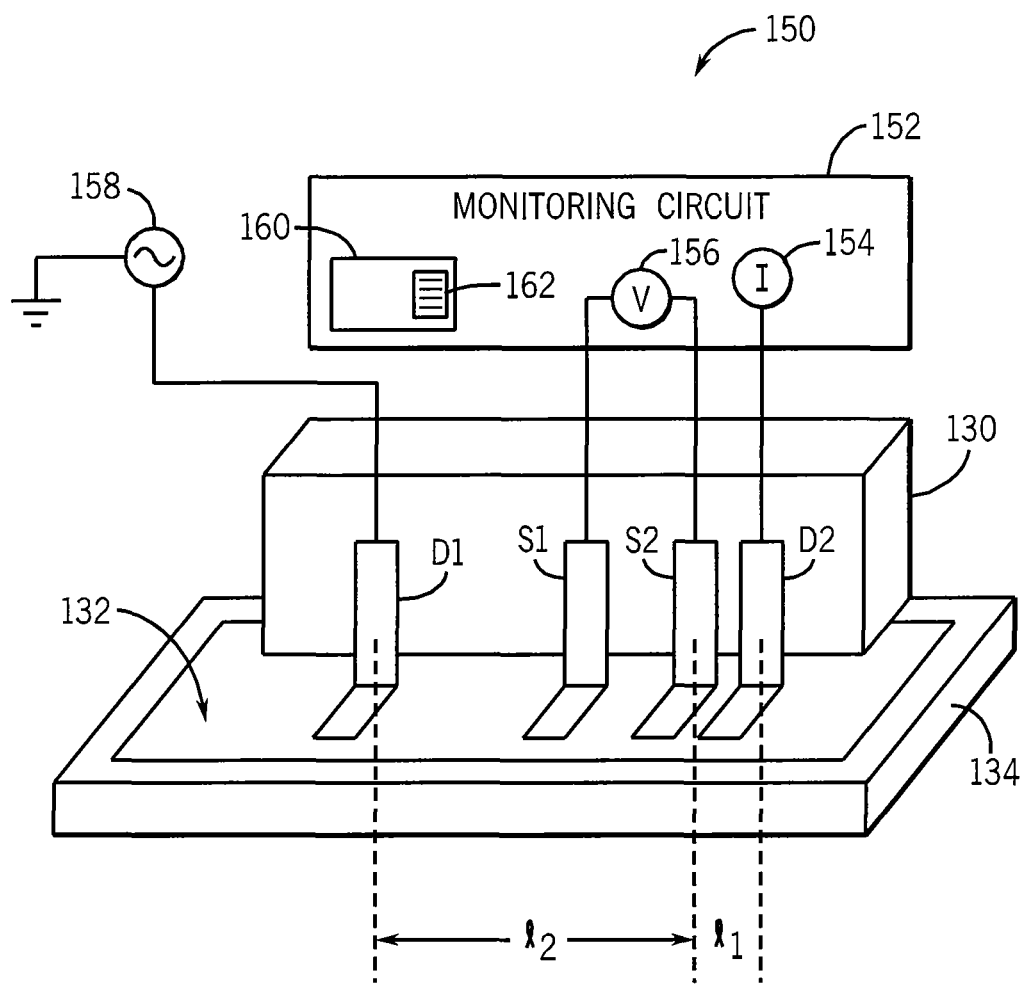
FIG. 10 is a tissue analysis apparatus according to the embodiment of FIG. 5 showing the tissue holder, electrodes, monitoring circuit and signal generator.

Referring now to FIG. 10, the arrangement of electrodes in impedance measuring apparatus 150 may have surface contact electrodes D1, D2, S1, S2 mounted on a holder 130 and in communication with tissue 132 which may be supported by tissue support 134. The fixture 130 holds the electrodes in a predetermined separation pattern. Importantly, the sensing electrodes S1, S2 are arranged between the driving electrodes D1, D2 and the separation of electrodes S2 and D2 by distance $l_1$ is much less than the separation of driven electrode D1 and S2 by distance $l_2$. Accordingly, $l_1$ is also much less than the separation of sensing electrodes S1, S2 as they are arranged between electrodes D1, D2. The impedance measuring apparatus 150 may also have a monitoring circuit 152 comprising a device to measure current 154 and a device to measure voltage 156. In addition, there may be a signal source 152 providing a voltage and/or current through driven electrode D1. An electronic computer 160 may be integrated into the monitoring circuit 162 (thereby receiving measurements from voltage and current devices 154, 156) and executing a stored program 162 to output a graph of tissue impedance measurements as a function of frequency.

The present invention has been described in terms of the preferred embodiment, and it is recognized that equivalents, alternatives, and modifications, aside from those expressly stated, are possible and within the scope of the appending claims.

The invention claimed is:

1. An apparatus for analysis of tissue comprising:
   a signal source producing an electrical signal including a range of frequencies;
   at least three electrodes positionable at separated points of electrical contact with the tissue;
   an electrical switch system connecting the signal source to different pairs of the at least three electrodes so that the electrical signal passes through different lengths of tissue:
   a monitoring circuit configured to communicate with the signal source to measure the electrical signal between an electrode pair connected by the electrical switch to receive the electrical signal;
   an electronic computer communicating with the monitoring circuit and configured to execute a stored program to:
   (a) measure the electrical signal between at least two different electrode pairs having different separation distances at corresponding points of electrical contact with the tissue;
   (b) use the measurements of the electrical signals at the different separation distances and use values of the different separation distances to provide an impedance measurement of the tissue between at least two electrodes corrected for electrode polarization;
   wherein the electronic computer performs the step of (b) by:
   determining at least two points of a function relating the measurements of the electrical signal to separation distance;
   extrapolating the function to a separation distance of zero; and
   correcting the impedance measurement of the tissue between at least two electrodes using the extrapolated value of the function.

2. The apparatus of claim 1 wherein the monitoring circuit measures a parameter selected from the group consisting of at least a current and a voltage.

3. The apparatus of claim 1 wherein the electronic computer outputs impedance measurements for multiple frequencies of the range of frequencies.

4. The apparatus of claim 1 wherein the electrodes are selected from the group consisting of treated electrodes, untreated electrodes, needle electrodes, and surface contact electrodes.

5. An apparatus for analysis of tissue comprising:
a signal source producing an electrical signal including a range of frequencies;
at least three electrodes at separated points of electrical contact with the tissue;
an electrical switch system connecting the signal source to different pairs of the at least three electrodes so that the electrical signal passes through different lengths of tissue;
a monitoring circuit configured to communicate with the signal source to measure the electrical signal between an electrode pair connected by the electrical switch to receive the electrical signal;
an electronic computer communicating with the monitoring circuit and configured to execute a stored program to:
(a) measure the electrical signal between at least two different electrode pairs having different separation distances at corresponding points of electrical contact with the tissue;
(b) use the measurements of the electrical signals at the different separation distances and use values of the different separation distances to provide an impedance measurement of the tissue between at least two electrodes corrected for electrode polarization; and
further comprising a fixture for holding the at least three electrodes in a known separation pattern and wherein the electronic computer determines the separation distances from stored values of the separation pattern of the fixture.

6. The apparatus of claim 5 wherein electrical switch system is electronically controllable and the electronic computer is configured to communicate with the electrical switch system to alternately connect the signal source to different pairs of the at least three electrodes.

7. The apparatus of claim 5 wherein the at least three electrodes are equally spaced in separation distance.

8. The apparatus of claim 5 wherein the at least three electrodes have different spacing to provide for different separation distances of pairs of the at least three electrodes, wherein the electrodes of the different separation distances do not include a common single electrode.

* * * * *